(12) United States Patent
Kuboki

(10) Patent No.: US 7,419,679 B2
(45) Date of Patent: Sep. 2, 2008

(54) MEDICAL IMPLANT HAVING A LAYER OF TITANIUM OR TITANIUM ALLOY FIBERS

(76) Inventor: Yoshinori Kuboki, 4-37, Nishino 8-jyo 1-chome, Nishi-ku, Sapporo-shi, Hokkaido (JP)

( * ) Notice: Subject to any disclaimer, the term of this patent is extended or adjusted under 35 U.S.C. 154(b) by 280 days.

(21) Appl. No.: 10/522,901

(22) PCT Filed: Jul. 31, 2003

(86) PCT No.: PCT/JP03/09758

§ 371 (c)(1),
(2), (4) Date: Feb. 1, 2005

(87) PCT Pub. No.: WO2004/012781

PCT Pub. Date: Feb. 12, 2004

(65) Prior Publication Data

US 2006/0073181 A1  Apr. 6, 2006

(30) Foreign Application Priority Data

Aug. 2, 2002  (JP) .............................. 2002-226690

(51) Int. Cl.
*A61F 2/00* (2006.01)
*C12N 11/14* (2006.01)
*A61C 8/00* (2006.01)

(52) U.S. Cl. ..................... 424/423; 433/201.1; 435/176

(58) Field of Classification Search ....................... None
See application file for complete search history.

(56) References Cited

U.S. PATENT DOCUMENTS

| | | | |
|---|---|---|---|
| 2,434,775 A | | 1/1948 | Sosnick |
| 2,553,016 A | | 5/1951 | Sosnick |
| 3,890,107 A | * | 6/1975 | White et al. ................. 428/613 |
| 4,812,404 A | * | 3/1989 | Kuboki et al. ................ 435/175 |
| 5,030,233 A | * | 7/1991 | Ducheyne ................ 623/23.54 |

FOREIGN PATENT DOCUMENTS

| | | |
|---|---|---|
| EP | 0 591 976 A1 | 4/1994 |
| JP | 63-109867 A1 | 5/1988 |
| JP | 05-269193 A1 | 10/1993 |
| JP | 08-140996 A1 | 6/1996 |
| JP | 11-000341 A1 | 1/1999 |
| WO | WO-01/25321 A1 | 4/2001 |

OTHER PUBLICATIONS

Johan W. M. Vehof, M.D. et al., "Ectopic Bone Formation in Titanium Mesh Loaded with Bone Morphogenetic Protein and Coated with Calcium Phosphate", Plastic and Reconstructive Surgery, Journal of the American Society of Plastic Surgeons, vol. 108, No. 2, Aug. 2001, http://www.plasreconsurg.org.

Y. Kuboki et al., "Rationale for Hydroxyapatite-coated titanium-mesh as an effective Carrier for BMP", Journal of Dental Research, 1988, vol. 77, Special Issue A, Abstract of Papers, 27th Annual Meeting of the AADR, 22nd Annual Meeting of the CADR, Mar. 4-7, 1998, Minneapolis, MN, The Official Publication of the International Association for Dental Research.

International Search Report for PCT/JP03/09758 mailed on Nov. 4, 2003.

* cited by examiner

*Primary Examiner*—David M Naff
(74) *Attorney, Agent, or Firm*—Cheng Law Group PLLC

(57) ABSTRACT

It is intended to provide a scaffold whereby a bone and a metallic material can three dimensionally form together a stereoscopic binding layer. Thus, a geometric space sufficient for cell actions is provided. As a result, the time required for the formation of a stereoscopic bond can be shortened and, moreover, a bond can be self-repaired owning to cell actions even in the case where a pair of the bond is injured by a wound, etc. As a material for designing a scaffold, titanium fibers of less than 100 μm in size and having an aspect ratio of 20 or more are selected. Then these fibers are entangled together to form a layer which is integrally fixed by vacuum sintering to a periphery surface of the various implant bodies, and coated with apatite. The fact that the layer contains spaces of an excellent ability to induce a biological hard tissue and fix the same is proved by the material, in which the layer is fixed to the periphery of an implant.

10 Claims, 9 Drawing Sheets (A) Two dimensional bonding of titanium and bone prepared by conventional method Plane bonding (B) Bonding of the titanium and bone using titanium non-woven cloth Three dimentional collaborational bonding of titanium and bone (A)

(B)

(A)

(B)

(A)

(B)

(A) Bone formation using titanium implant with beads (B) Natural healing bone formation (A)

(B)

(A)

(B)

MEDICAL IMPLANT HAVING A LAYER OF TITANIUM OR TITANIUM ALLOY FIBERS

FIELD OF THE INVENTION

The present invention relates to a biological hard tissue inductive scaffold material composed of titanium or titanium group alloy fiber which is used together with an implant such as an artificial root of the tooth or an artificial joint implant, a method for preparation thereof and a cell culture proliferation reactor in regenerative medicine engineering.

DESCRIPTION OF THE PRIOR ART

In general, in the field of oral surgery or orthopaedic surgery, as a material for implant to be implanted in an organism, a product made of metallic material such as an artificial root of the tooth or an artificial joint are conventionally used. Recently, among these metallic materials, the uses of titanium and titanium alloy are remarkably becoming frequent. The reason is that, in comparison with other metals, titanium has an excellent properties including rare antigenic function in an organism, relatively small specific gravity and strong mechanical strength. Further, at the MRI examination of a patient to whom a metallic material is implanted, if the metallic material has magnetic property, various problems cause. On the contrary, titanium which does not have magnetic property, is superior at this subsidiary effect, and this is one of the reason why titanium is admirably used.

In particular, the uses of a medical material composed of titanium or titanium group alloy are broadly increasing in the field of orthopaedic surgery or dentistry. Accordingly, metallic material which does not have antigenic function acts good function in an organism, and contributes to the improvement of QOL of a postoperative patient.

However, the medical material composed of titanium or titanium group alloy is not sufficiently satisfied. For example, even if there is no antigenic function, at a contact surface of a titanium metallic material with an organism, in some occasions, sheath tissue is formed by gathering fibroblasts of connective tissues with collagenous fiber on the surface of material even if it is implanted in a bone tissue. Therefore, when a titanium metal material can not contact directly with a bone tissue, there is a problem that it is difficult for the bone tissue and the metallic material to become an one body.

To dissolve this problem, recently, improvement by coating hydroxy apatite on the surface of titanium is carried out, while improvement to have complicated structure on the surface by forming a structure considering an inductivity and stickiness of bone tissue, that is, forming convex and concave structure on the surface of the material or to stick many fine beads on the surface are carried out. However, by these means, the biological and mechanical bonding of the metal material with bone tissue is not sufficient. Even if the metal material and bone tissue can be observed to be bonded, when a breaking starts from a marginal part, the breaking can not be restored and extends to whole part, causes loosening and falls down in early stage. These instances are becoming clear by repeating many cases. Therefore, in cases of aged patients, very dangerous phenomena that the dissociation between the material and bone tissue progresses gradually are frequently observed. Further, since it is necessary to progress 3 to 6 months to complete the bonding of the metallic material with bone tissue, a problem that the next step treatment can not be started is actually pointed out.

For dissolution of above problem, recently, together use of BMP (Bone Morphogenetic Protein) which accelerate the induction of osteoblasts or BMP relating to the induction of other cells with medical materials e.g. implant made of titanium is carried out. Together use with these physiological functional activators is effective, and migration of osteoblasts can be observed closely to the titanium metallic material, however, the formation of cells of tissue status called as osteointegration characterizing that material and bone are becoming one body can not easily be observed.

In the meanwhile, as the aforementioned improved technique for trial to make the surface of material complicated shape, the following method is proposed. That is, the technique to wind up at random and accumulate fine fibers made of titanium or titanium alloy surround the core part of implant to be implanted into vivo bone, to form a compressed body of desired shape and dimension by compressing to the core direction and to prepare a dentistry implant made of titanium having buffering function by combining the body with the core are proposed (Japanese Application Publication H8-140996). As the specific example of fine fibers, fine fibers having 0.1 mm to 0.7 mm diameter, desirably fine fibers having 0.3 mm to 0.5 mm diameter are indicated. The meaning of "body" formed by the titanium fibers is to perform a buffering function by accepting outer strength, namely occusal strength, elastically to the all direction, further to accept the migration and proliferation of vivo bone tissue from many pore gaps so as to improve the stickiness to the bone of the implanted part and to assume better stability of the implanted part.

Furthermore, a process to produce "pore structure" by pouring a mixture of metal and an foaming agent in a mold, heating to the temperature higher than melting point under pressing condition and by releasing the pressure air at adequate period (U.S. Pat. No. 2,553,016), and as developing embodiment of this process, a process to generate the mercury vapor or to generate a specific gas by decomposition of hydroxide or carbide of titanium or zircon (U.S. Pat. No. 2,434,775 and U.S. Pat. No. 2,553,016) are proposed. And an orthopaedic implant which attempts to combine bone tissue and an implant by obtaining thin layer of metal "pore structure" by specific foaming methods characterizing to generate pores at the melting state of metal which are mentioned above, adhering said thin layer to the surface of the implant and inducing bone tissue into pore cells after implanted into organism is proposed (Japanese Application Publication H11-341). As an example of metal used in above processes, various metals such as pure titanium, titanium alloy, stainless steel, cobalt-chrome alloy or aluminium are disclosed. And, also disclosed that the size of opening formed by pore is in the limitation of 0.5 mm to 1.5 mm, further that the "pore structure" is to be formed by thin layer of 1.5 mm to 3 mm thickness.

The former proposal is basically to prepare one titanium filament of 0.1 mm to 0.7 mm diameter, to wind it up around the implant core, and to compress so as to form porous gaps which permit migration and proliferation of neogenesis bone tissue between accumulated filaments. However, it is obvious that there is a limit for the formation of the porous gaps. That is, this method is to wind up the fiber material and to compress the fiber material in the core direction so as to equip the fiber material to the core, and the possibility to adjust porous gaps is small. If the fiber material is wound not so tightly aiming to secure certain gaps, the problem that the equipping of the fiber material to the core becomes difficult occurs. Namely, since there is a limitation to attempt migration and proliferation of bone tissue by above mentioned method, sufficient osteointegration tissue is not formed.

Further, regarding the latter proposal, since the "pore structure" is controlled by "amount of gas and shape" to be supplied to melted metal, it can not be said that the controlling of the size of cell, distribution of pores and thickness of wall which have influence directly to migration, adhesion and proliferation of osteoblasts is not so easy. The size of opening formed by pore disclosed in the proposal is in the limitation of 0.5 mm to 1.5 mm, and the thickness of wall of cell can be presumed from the scale of attached drawing as same as to the size of opening formed by pore or more. This thickness of wall of cell is not so remarkably different from that of the fine beads method based on the diameter of fine beads which is a prerequisite art of this proposal, therefore, it is difficult to expect good affinity with bone cells so as to bring formation of one body with tissue.

As mentioned above, in the previous methods that use titanium or titanium group alloy, which are recognized to have good affinity with organism tissue, there are several problems in aforementioned points, in particular, the formation of sufficient tissue in which bone tissue and titanium material become one body, namely so called osteointegration is not accomplished. After operation, loosening of bond between bone and titanium occurs from a marginal part, and in many cases the loosening is led to falling down of a tooth in early stage. A patient is feeling discomfort during the process before the falling becomes inevitable. That is, many problems are pointed out. In the cases of conventional artificial root of the tooth or artificial joint which are actually used in medical field, the bond of bone with metal is plane as shown in FIG. 1 (A) and it needs from 3 months to 6 months to accomplish enough bonding strength, therefore it is necessary to keep rest during this period and is impossible to progress to the next step. This point will be illustrated in the drawing mentioned later. The reason responding to said problem can be explained as follows, that is, the field in which cells act to accomplish the bond with metal is only two dimetional plane formed between planes of each subject to be bonded and can be said as a simple and minimized plane.

As mentioned above, the conventional methods of using such as titanium metal material are aiming to bond bone tissue with an implant made of metal by two dimensional plane, and said conventional arts called it as osteointegration. However, from the biological viewpoint, there is a problem of preservation for long term. The object of the present invention is to provide a biological hard tissue inductive scaffold material which can induce the tissue layer of hybrid state by three dimensionally cooperating an implant material with bone tissue of organism side by using an implant to be replaced to various hard tissues which do not have above problems.

Further the object of the present invention is to provide a method to accomplish the bonding of a metal material with bone within one month, in contrast to the conventional method which takes 3 to 6 months to accomplish the bonding of a metal material with bone. This is proved in Example 3 mentioned later.

Furthermore, in the regenerative medicine engineering of today, it is actually required to carry out the trial to prompt the rapid proliferation of active cells including bone cells by introducing osteoblasts or stem cells with a physiological active material to the replacing material for hard tissues. That is, a material which can be used as a bioreactor for cell cultivation, which is characterized that the physiological active material or stem cells can be surely kept for a certain period, timed-releasability can be displayed and having good affinity to cells is required. Said bioreactor with the cells can be implanted in tissue of a human body as a whole, the proliferated cells are separated and can be supplied to a researching facility where the proliferated tissue is needed or to a medical facility immediately. To said requirement, the conventional material is not the material which can satisfy the requirement sufficiently.

SUMMARY OF THE INVENTION

The present invention is to develop and to provide a material which can respond to the above mentioned requirement, that is, can be used as the scaffold material effective to a biological hard tissue, further, can be used as a bioreactor effective to cells besides the hard tissue.

The inventors of the present invention have carried out intensive study as illustrated below, and have made it clear that osteoblasts can be easily migrated to fine fibrous material of titanium metal and proliferates, that is, has good affinity with it, and there is high correlation between diameter of fiber to be used and proliferation action of cells, and have obtained a series of important knowledge based on the knowledge, and have developed and proposed the material which can respond to said requirement.

That is, the inventors of the present invention have investigated intently about the cultivation condition which osteoblast like, and have made it clear that osteoblast grows in geometric space composed by very fine fibers. By continuing further basic investigation, the inventors of the present invention have obtain the following knowledge, that is, osteoblast indicates very high affinity to titanium fiber, and specifically, in the geometric space composed by a mass of titanium fiber having smaller diameter than 100 µm and extend of it is from 100 to 400 µm indicates higher affinity and have a specific property to stick more actively than that of titanium fiber having larger diameter than 100 µm.

A part of medical results of these series of knowledge were already reported in "Densitry in Japan" vol. 37, page 42-50, 2001, "J. Bone and joint surgery" 93A, S1-105 to 115, 2001, "J. Biochemistry", Vol. 121, page 317 to 324, 1997 (not all results as disclosed in the present invention, and the method for dissolving of the problem is not reported).

The inventors of the present invention have expanded the property of fiber actively obtained from above mentioned knowledge and from the view point that the one body tissue of hybrid state composed of bone tissue, metal fiber and an implant can be induced by arranging the fibers surrounding the metal implant, have repeated various experiments and have made it clear that the aimed result can be obtained.

As aforementioned, in the cases of an artificial root of the tooth or an artificial joint, since the bonding of bone with metal is plane, it takes from 3 to 6 months to accomplish a bonding tissue with sufficient strength and it is necessary to keep rest during this period and is impossible to progress to the next step. However, by the present invention, the three dimensional complicated space formed by titanium fibers is provided, namely in the case of a layer of 2 mm thickness, the surface area is more than 20 times larger than that of plane, consequently the space where cells can act is provided, and it become clear that osteointegration of bone tissue can be accomplished in short period together with the acceleration effect of action of cells.

Further, by the continuation of investigation, it becomes clear that the induction and proliferation of cells can be possible on other cells besides osteoblasts. That is, when the titanium fiber having smaller diameter than 100 µm, it is understood that various kind of cells are induced into fiber layer and stick actively and grow. That is, the inventors of the present invention have succeeded to provide a medical material composed of metal implant material having high affinity to whole tissue of organism by use of the fine titanium fiber.

Even if the hybrid with an implant is formed by inducing cells into fiber layer utilizing high affinity of cells to titanium fiber layer composed of titanium fiber having said specific diameter, the morphological stability is required when it is used by implanting into human body. The inventors of the present invention have investigated this point and have accomplished the following process. That is, the titanium fibers are accumulated at random and form a layer, then is sintered by alone or by winding up to an implant in vacuum condition. The cross points of fibers each other and contacting points of the fibers with the implant are fused at the spots and forms a rigid structure. The outer strength loaded to the layer is dispersed to many fused points, and forms the subject of rigid structure with good morphological stability having sufficient strength. Further, after fused, it is found that the affinity of bone cells to the tissue of organism is not affected by fusing process at all.

As the method to stick or fix metal fibers, soldering method or silver soldering method can be mentioned, however, in these methods paste is generally used. And, since the paste has a possibility to contain harmful component to cells, this method can not be said as an adequate method. Aforementioned sintering method in vacuum condition is selected from various fusing and sticking methods considering this point and the effectivity of it is found out. The sintering in vacuum condition does not use harmful subject to cells and does not generate harmful subject to cells. But, if there is another method which is effective to stick fiber each other, that is, there is a fusing method which does not affect the growth of cells, tissue or human body, there is no problem to adopt the method and is contained in the scope of the present invention.

The inventors of the present invention have carried out more intensive study and found out that bone cells can be more effectively induced by accelerating the implantation of osteoblasts by depositing crystal of hydroxyl apatite or hydroxyl apatite containing apatite carbonate on the surface of fiber of titanium metal layer, or by previously sticking physiological functional activator such as various cytokine e.g. BMP (Bone Morphogenetic Protein) or cell growth factor component which accelerate the growth of osteoblasts. Such function and effect are not provided simply by the function of the treated component, but is provided by together use with fine titanium fibers. Further, it becomes clear that function and effect with remarkable preserving ability and times-releasing ability is provided and generated.

When said function and effect are compared with that of a plane subject, there is remarkable difference. This difference is considered to be caused by remarkable difference of surface area compared with that of plane subject. That is, even if the loading amount is same, the loading state does not bias and loaded homogeneously to the broad area, further, the loading area is improved and consequently the total loading amount is improved. Further, the function of the physiological active material acts more broadly, because very fine fibers of less than 100 μm diameter is used instead of a plane subject with small surface area, and accordingly induces osteoblasts effectively and can form strong one body tissue of organism.

As the method for loading of this case, above mentioned BMP component, cytokine, various cell growth factor component or factor having an activity of organism can be stuck directly to the metal fiber. However, it is effective to contain a subject which can be absorbed in organism such as polyglycolic acid, polylactic acid, copolymer of polylactic acid-polyglycolic acid, biodegradable (3-hydroxylbutyl-4-hydroxylbutylate) polyester polymer, polydioxane, polyethyleneglycol, collagen, gelatin, albumin, fibrin, chitosan, chitin, fibroin, cellulose, mucopolysaccharide, vitronectin, fibronectin, laminin, alginic acid, hyaluronic acid, heparin, heparan sulfate, chondroitin sulfate, polyamino acid, dextran, agarose, pectin, mannan and derivatives thereof between fibers of titanium or titanium compound, then to adsorb above mentioned factors to the absorption subjects in organism.

The inventors of the present invention have clarified that if it is possible to control the behavior of cells, namely, the behavior that the cells can easily adhere to fine fibers, by controlling said bioactive materials, the time and the position to induce and to activate cells can be voluntarily controlled and can be used as one of effective embodiments. Of cause, said behavior of cells can be concluded as the essential property which cells have themselves not by use of said bioactive materials.

By using the embodiment that fibers are entangled at random, cells migrate positively into gaps between fibers arranged at random, and a strong three dimensional hybrid structure characterizing that cells and metallic fibers are complicatedly entangled is formed. And in the case, when the structure is needed to be reinforced to a specific direction, it is possible to use a woven cloth and it is not to limit the scope of the present invention.

The case to apply above mentioned metallic fiber layer to a human body or other animal body, for example, if an implant metal material is implanted in bone tissue, cells to generate a blood vessel and a bone into three dimensional gap composed of metallic fiber layer equipped to the implant, generate a hybrid structure and metal material and bone tissue becomes one body, as illustrated above. Accordingly, anchor effect of an implant metal material becomes stronger and the metal material becomes to be fixed strongly in the bone tissue. It becomes clear that for the rapid formation of said anchor effect by invading and fixing of cells and blood vessel, the use having titanium fibers of specific diameter and of specific aspect ratio is necessary and is the unexpected action and effect.

This knowledge is the result obtained by many actual experiments (several hundred cases), and the investments considering the relationship between diameter of fine fiber of specific metal (titanium or titanium group alloy) and cells is carried out by the inventors of the present invention as the first time and is very creative and novel. And by using the fine fibers, remarkably excellent action and effect are provided, consequently, the present invention contributes largely to the growth of medicine and the welfare of the human beings. The metal material as an implant to which the scaffold material of the present invention is equipped is used in these experiments, is referring to a medical implant made of titanium metal used in medical field because of necessarily to refer the affinity with bone, however, of cause, it can be used for a medical implant made of other metal or non-metallic material.

Further, the inventors of the present invention have clarified from various experiments that, to the titanium fiber of less than 100 μm diameter, various kinds of cells besides osteoblasts actively acts physiologically same as to osteoblast and possesses a property to adheres positively. Of cause, in which a stem cell which is called as an universal cell is contained. That is, from this fact, the inventors of the present invention have clarified that the titanium metal fiber layer of less than 100 μm diameter has a function for a cell cultivate and proliferation material in regenerative medical engineering, and can be used as a cell culture proliferation reactor.

DESCRIPTION OF THE PREFERRED EMBODIMENT

Figure 1:
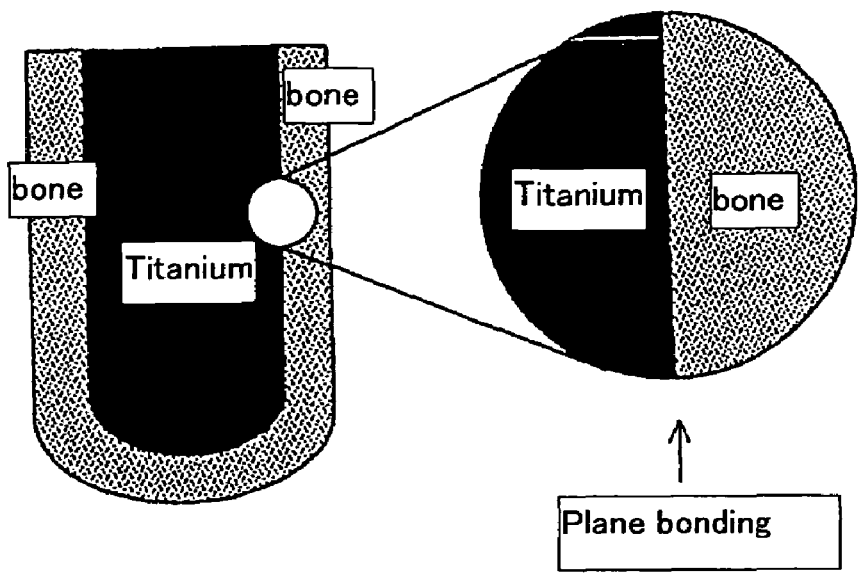
FIG. 1 is a schematic view and the partial enlarged view of a conventional implant (A) and an implant of the present invention composed of a titanium rod and non-woven cloth of titanium fibers, which was fused to the surface of the rod by vacuum sintering (B).
Figure 1:
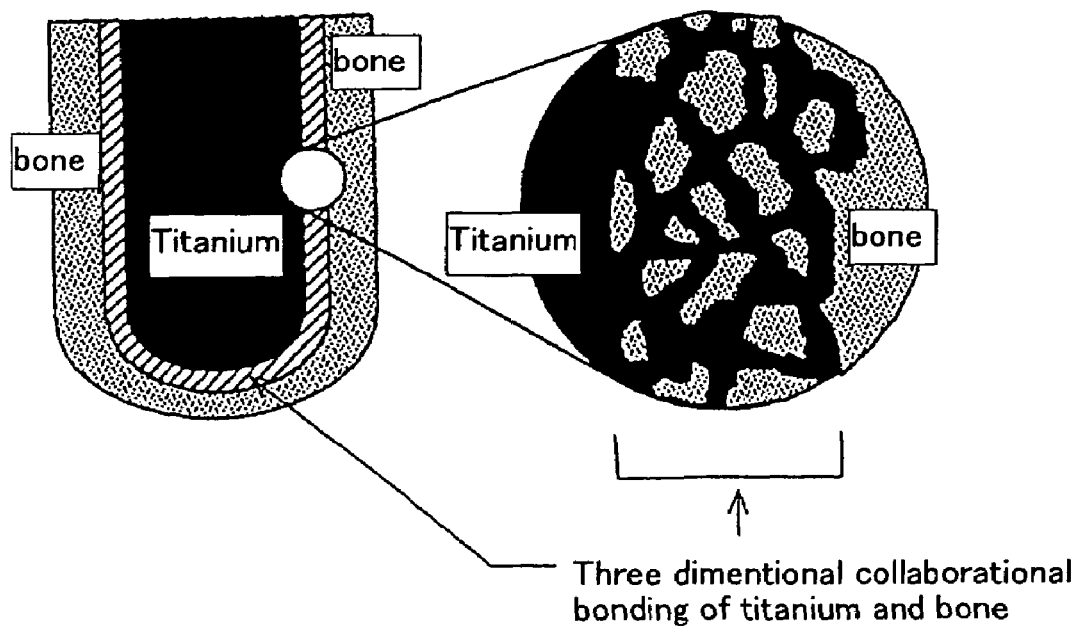

Considering abovementioned series of knowledge, the inventors of the present invention have dissolved the problems mentioned above by carrying out subjects recited in (1)-(13).

(1) A biological hard tissue inductive scaffold material to be used with various implants comprising, titanium or titanium group alloy fiber, wherein said biological hard tissue inductive scaffold material is materially designed to excel in biological hard tissue inductivity and fixing ability, said titanium or titanium group alloy fiber is selecting a fiber whose average diameter is 100 µm or less and aspect ratio is 20 or more, (short axis:long axis ratio=1:20 or more), and said fibers are accumulated to form a layer so as to form an implantation space for biological hard tissue from the surface to inside.

(2) The biological hard tissue inductive scaffold material of (1), wherein a layer shaped scaffold material comprising said fibers or various implants to be used with said scaffold material are sintered in vacuum so as crossing points or contacting points of the fibers each other or the fibers and the implant to be fused and fixed.

(3) The biological hard tissue inductive scaffold material of (1) or (2), wherein the surface of said fibers is treated with apatite forming liquid and coated with calcium phosphate compound containing hydroxyapatite or carbonate apatite.

(4) The biological hard tissue inductive scaffold material in accordance with anyone of (1) to (3), wherein the surface of said fibers is treated with treating liquid containing a physiological active material or a physiological activation promoter which activates cells.

(5) The biological hard tissue inductive scaffold material of (4), wherein the physiological active material or a physiological activation promoter which activates cells is at least one selected from the group consisting of cell growth factor, cytokine, antibiotic, cell growth controlling factor, enzyme, protein, polysaccharides, phospholipids, lipoprotein or mucopolysaccharides.

(6) The biological hard tissue inductive scaffold material in accordance with anyone of (1) to (5), wherein the implant is an artificial root of the tooth having an embedding part and the layer which is winded and compressed around the embedding part to integrally fixed to the embedding part.

(7) The biological hard tissue inductive scaffold material in accordance with anyone of (1) to (5), wherein the implant is an artificial joint having an embedding part and the layer which is winded and compressed around the embedding part to integrally fixed to the embedding part.

(8) The biological hard tissue inductive scaffold material in accordance with anyone of (1) to (5), wherein the implant is an implant for bone repairing having an embedding part and the layer which is winded and compressed around the embedding part to integrally fixed to the embedding part.

(9) The biological hard tissue inductive scaffold material in accordance with anyone of (6) to (8), wherein the integral formation of embedding part with the layer is carried out by sintering in vacuum.

(10) A method for preparation of the biological hard tissue inductive scaffold material comprising, forming a layer by entangling titanium or titanium group alloy fibers whose average diameter is smaller than 100 µm and aspect ratio is 20 or more, winding up the layer to the artificial root of the tooth or an artificial joint, and sintering it in vacuum so as to fuse the crossing points or contacting points of the fibers each other or the fibers and the implant.

(11) A cell culture proliferation reactor in regenerative medical engineering comprising, using titanium fibers whose average diameter is 100 μm or less and aspect ratio is 20 or more, (short axis:long axis ratio=1:20 or more), or further treated with apatite forming liquid and coated with calcium phosphate compound containing hydroxyapatite or carbonate apatite. And said fibers are accumulated to form a layer so as to create a space for growing of biological hard tissue from the surface to inside, excelling in biological hard tissue inductivity and fixing ability.

(12) The cell culture proliferation reactor in regenerative medical engineering of (11), wherein the layer of fibers is treated with solution containing a physiological active material or a physiological activation promoter which activates cells.

(13) The cell culture proliferation reactor in regenerative medical engineering of (11), wherein the physiological active material or a physiological activation promoter which activates cells is at least one selected from the group consisting of cell growth factor, cytokine, antibiotic, cell growth controlling factor, enzyme, protein, polysaccharides, phospholipids, lipoprotein or mucopolysaccharides.

In the present invention, the wording of "fibers are accumulated to form a layer" means to accumulate woven cloths having network space to form a layer or to accumulate non-woven cloths prepared by entangling fibers to form a layer. And the purpose to create a space for growing of biological hard tissue from the surface to inside and to materially design excelling in biological hard tissue inductivity and fixing ability can be accomplished by the formation of non-woven cloth layer by entangling titanium fibers whose average diameter is 100 μm or less and aspect ratio is 20 or more at random, and space formed by said non-woven cloth has an opening which permits the migrating of cells and the space sufficient for proliferation of the migrated cells. In the Examples mentioned below, said fiber layer is referred using void fraction and density, and biological hard tissue inductivity and fixing ability are effective in very broad range. The present invention can set up excellent space to biological hard tissue by restricting the thickness of fibers to 100 μm or less and excels in processability, therefore is advantageous compared to the case which uses thicker fibers. Additionally, the present invention has a significant meaning at the cell size level technique, besides the difference of apparent thickness.

EXAMPLE

The embodiments of the present invention are illustrated based on the Examples and drawings disclosed in following heterotopic bone forming experiments, homotopitic bone forming experiments, apatite coating experiments or cell proliferating experiments. These Examples are disclosing specific examples for the easy understanding of the present invention and not intending to limit the scope of the claims of the present invention.

The scaffold material used in following experiments is the material prepared by the process mentioned below. That is, preparing a layer represented by non-woven cloth formed by entangling titanium metal fibers or titanium group alloy fibers and whose average diameter is 100 μm or less and aspect ratio is 20 or more at random, winding said layer around the outer periphery of a titanium implant material and sintering them in vacuum so as crossing points or contacting points of the fibers each other or the contact points of fibers and the implant to be fused and fixed, then carrying out a treatment of apatite coating. Relationship between a conventional titanium implant and a bone tissue grown around said implant and relationship between a titanium implant around which the scaffold of the present invention composed of titanium fibers layer (non-woven cloth) and a bone tissue grown around said implant are shown respectively in FIG. 1.

(A) shows an titanium implant prepared by a conventional method and a bone tissue grown around said titanium implant and bone tissue grown around the implant can be observed (left side drawing), however, from the enlarged drawing (right side drawing) it is understood that bone tissue is only bonded plane to the implant. On the contrary, (B) is the drawing showing the relationship between an implant to which scaffold of the present invention is set up and bone tissue grown around said implant (left side drawing), the bone tissue is induced into a fiber layer in which fibers are entangled three dimensionaliry, bonded with the three dimensional and complicated structure and continued to the outer bone tissue through this bonding layer. That is, compared with (A) by conventional implant, it is clearly understood that the rigid bone tissue structure based on the anchor effect by the complicatedly entangled fibers and the space formed by said complicatedly entangled fibers, that is osteointegration is three dimentionaliry accomplished.

Example 1

Heterotopic Bone Forming Experiment Under the Skin of Rat

I. Preparation of a Specimen for Experiment: Following Examples ① and ② are Prepared:

① Preparing a non-woven cloth of 85% void fraction and 0.9 g/mL density composed of titanium metal fiber having 8 μm-80 μm diameter and 20 or more aspect ratio (product of Bekinit Co., Ltd.). This non-woven cloth is wounded firmly to a titanium rod by a voluntarily thickness, and a composite consisting of titanium non-woven cloth and a titanium rod of 1.5 mm diameter is prepared. Said composite is filled in a sintering syringe made of ceramics and sintered at 1000° C. for 5 hours in high vacuum condition. Consequently, at many contacting points of fibers themselves and contacting points with titanium rod surface, fibers are fused. And thus the rigid composite which does not sink or does not cause the transformation of shape by adding forth on the surface is prepared.

② A titanium metal rod having 1.5 mm diameter.

II. Method for Implanting Experiment:

1. A composite corresponding to the scaffold material of above mentioned specimen ① of the present invention and a metal rod corresponding to the implant in conventional technique of above mentioned specimen ② are respectively implanted with S-300BMP, which is bone forming protein extracted from cow bone and purified, under the skin of a rat and the bone forming experiments for 4 weeks are carried out. After 4 weeks the difference between said two specimens are observed by a microscope histologically and quantitative analysis of Ca stuck to metal rod is carried out.

Figure 2:
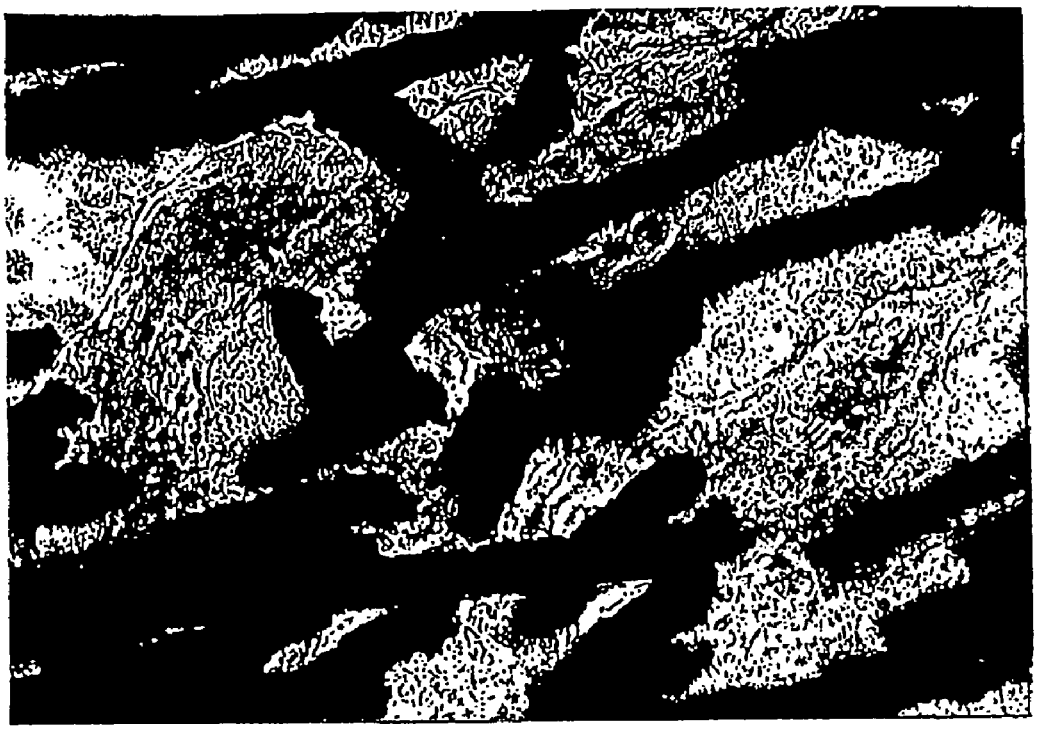
FIGS. 2 (A) and 2 (B) are comparative microscopic pictures of the BMP induced heterotopic bone formation in rat subcutaneously using two materials as the carrier of BMP as the result of active bone formation when a metal rod alone was implanted.
Figure 2:

III. Experimental Results:

Results by microscopic observation are shown in FIG. 2. In the case of a composite specimen ① prepared by sintering a non-woven cloth made of metal titanium in vacuum, which is the scaffold material of the present invention, the state of formation of bone after 4 weeks is shown in FIG. 2 (A). In FIG. 2 (A), osteoblasts are infiltrated and induced into said non-woven cloth and the formation of vigorous bone structure which is complexly complicated is observed. On the contrary, results by titanium metal rod alone, namely, to which non-woven cloth is not wound, is shown in FIG. 2 (B). From FIG. 2 (B), the formation of bone tissue characterizing that said two are becoming three dimensionalily one body is not observed and at the interface of rod (black part) and bone (white part) there is no bonding to connect these two, and the rod and bone are only existing independently holding said interface between.

Figure 3:
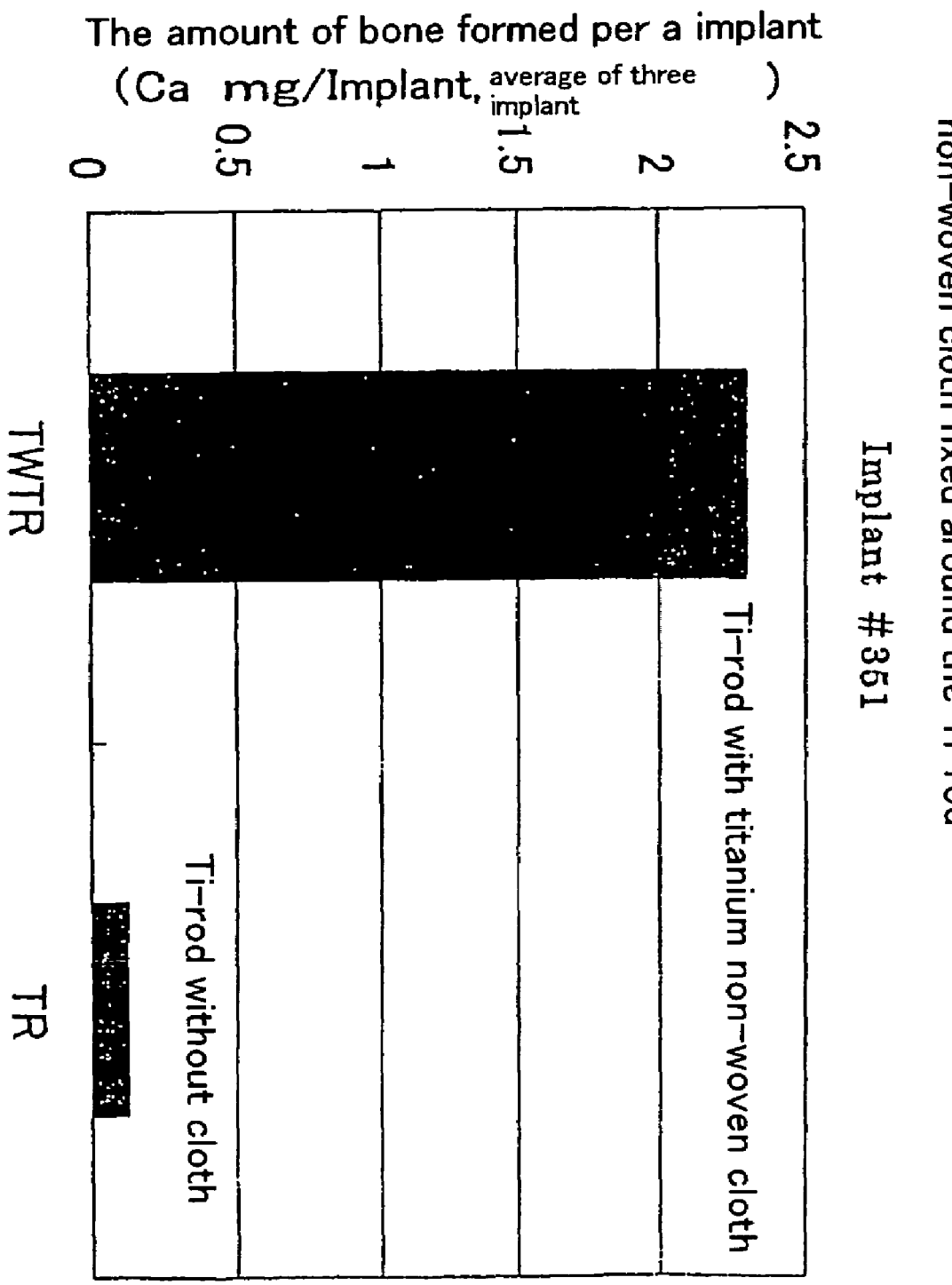
FIG. 3 is the drawing showing the different in amount of bone formation when the two materials were implanted into rat subcutaneously. "TWTR" indicates that the amount of bone formation when a scaffold of the present invention which composed of metal root and a non-woven cloth of titanium fibers, which was fused on the surface of the rod, was implanted with BMP. "TR" indicates amount of bone formation when a metal rod alone was implanted with BMP. Bone amounts are examined 4 weeks after implantation and expressed by calcium contents.

Further the results by Ca quantitative analysis are shown in FIG. 3. That is, in the case specimen ① when titanium non-woven cloth is wound around the titanium rod having 1.5 mm diameter, it becomes clear that 2.3 mg of Ca in average is stuck to one implant. While in the case of specimen ② which does not wound titanium non-woven cloth, the sticking amount is only 0.13 mg, and there is obvious difference between these two, and the difference is almost 18 times.

Example 2

Experiment to Confirm the Effect of Hydroxyl Apatite Coating Treatment to the Formation of a Heterotopic Bone Experimental Method:

After titanium non-woven cloth is put on a titanium rod having 1.5 mm diameter without sintering in vacuum following two composites are prepared. That is, apatite coated composite ③ prepared by a liquid dipping method which is an apatite coating treatment disclosed in Example 4 mentioned later, and non apatite coated composite ④ are prepared. These composites are implanted under the skin of rat for 4 weeks and the difference of bone tissue formation between these two composites is compared.

Figure 4:
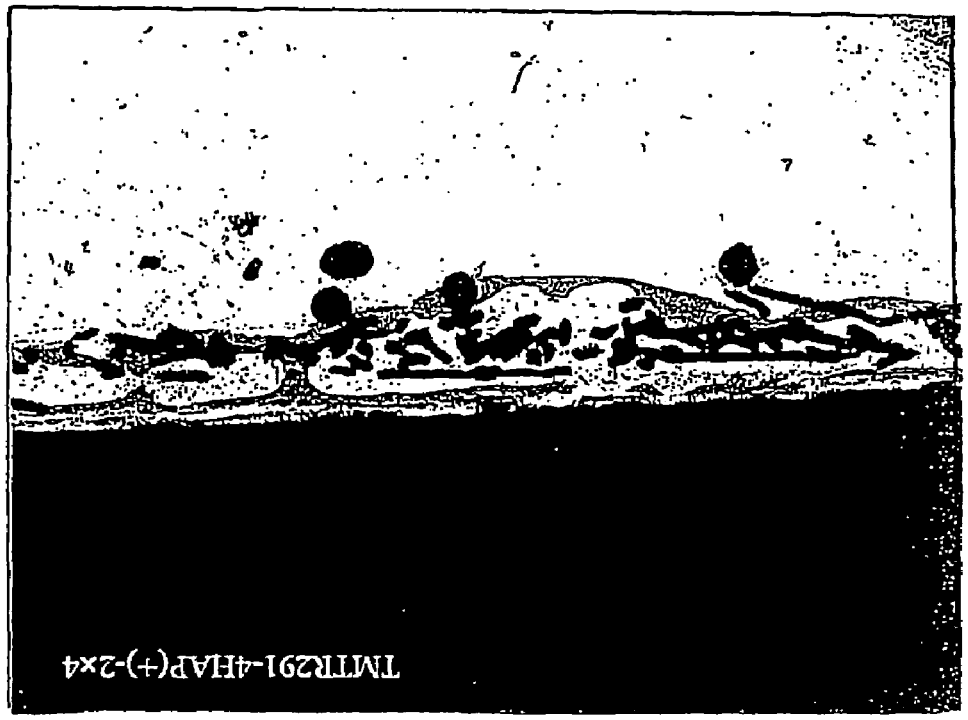
FIG. 4 is a comparative microscopic picture of the BMP induced bone formation in rat skin when the two materials as follow were used as BMP carriers. A: s titanium rod simply attached with a non-woven cloth of titanium fibers with apatite coating. B: the same material as A, but without apatite coating. The former shows very active bone formation (bone is clearly distinguished by red color or as thicker and fused contour by gray or black color), but the latter poor. Both materials were examined 4 weeks after implantation.
Figure 4:

Experimental Results:

Results are shown in FIG. 4. In the apatite coated composite ③, vigorous bone formation is observed at the titanium non-woven cloth part. Bone is clearly distinguished as the red colored areas or as thicker and fused contour in gray or black [FIG. 4 (A)]. However, since the titanium non-woven cloth is not treated by sintering in vacuum at the surface of the titanium rod, these two are not united in one body and the growth of bone is not observed on the surface of rod, while bone is formed in the fiber space slightly apart from the surface of rod [FIG. 4 (A)].

On the contrary, in non apatite coated composite ④ bone is not formed at all [FIG. 4 (B)]. That is, from this heterotopic bone forming experiment, it becomes clear that the apatite coating treatment is acting very important role in the formation of bone. Further, the experimental results of the specimen ① characterized that a titanium metal rod and titanium non-woven cloth is fused by sintering in vacuum of Example 1 and of the composite ③ characterized that a titanium metal rod and titanium non-woven cloth is not fused by sintering in vacuum of Example 2 clearly indicate that it is important that titanium non-woven cloth is previously fused to a titanium metal rod to form one body by sintering in vacuum. That is, this sintering treatment in vacuum contributes not only to mechanical strength of the composite, but also to the improvement of the effect for bone formation, and acts very important role.

All experiments described in Examples 1 and 2 are heterotopic bone forming experiment under the skin of rat, and the object of these experiments are to confirm and investigate the significance of equipping with titanium non-woven cloth by bone forming experiments at the tissue except bone, and summarized in Table 1.

TABLE 1

Summary of experiments described in Examples 1 and 2

| Composite | indication by marks | formation of bone |
|---|---|---|
| Titanim rod (TR) alone | TR | – |
| TR and titanium non-woven cloth (TM) | TR + TM | + or some times – |
| TR + TM and apatite Coating (HAP) | TR + TM + HAP | + + + |
| TR + TM + HAP and sintering in vacuum (SIN) | TR + TM + HAP + SIN | + + + + |

Example 3

Orthotopic Bone Forming Experiment in Head Bone of Rabbit

I. Experimental Method

Experiments are carried out according to the procedures 1, 2 and 3 mentioned below.
1. A rabbit of 2.5 kg weight is anesthetized by nenbutal intravenous anesthesia, and perioste of head bone is partially incised and a hole of 3 mm diameter and 3 mm thickness which passes through the calvarial bone is dug at the parietal area by a diamond round disk for dental use.
2. A titanium rod equipped with titanium non-woven cloth (cut off to cylindrical shape of 3 mm diameter and 3 mm thickness) is inserted into the hole and perioste and dermis is closured.
3. The rabbit is killed after 4 weeks and the bone at the parietal area is removed and embedded by resin, then a ground specimen of 20 μm thickness is prepared. The specimen is dyed by hematoxylin-eosin dying method.

Figure 5:
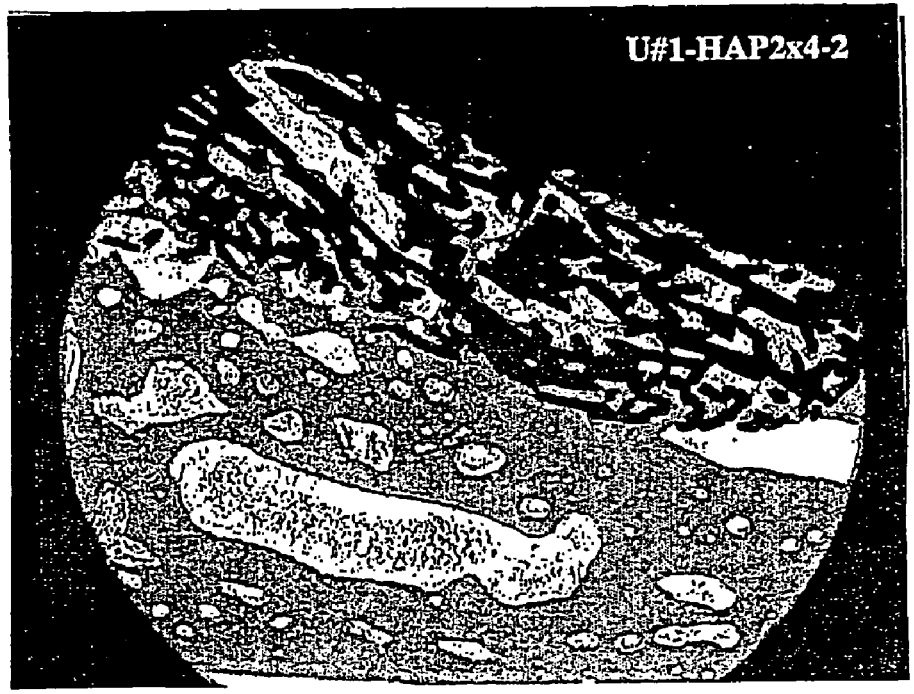
FIG. 5 is comparative microscopic picture of the amount of bone formation when the two materials as follow were implanted into the bone defect in the cranium of rabbits. A: a scaffold of the present invention, which composed of titanium rod and a non-woven cloth of titanium fibers, which was fused by vacuum sintering on the rod and then hydroxyapatite coated. B: the same material as A, but without apatite coating on the surface. The former shows active bone formation within the non-woven cloth, but the latter very poor. Both materials were examined 4 weeks after implantation.
Figure 5:
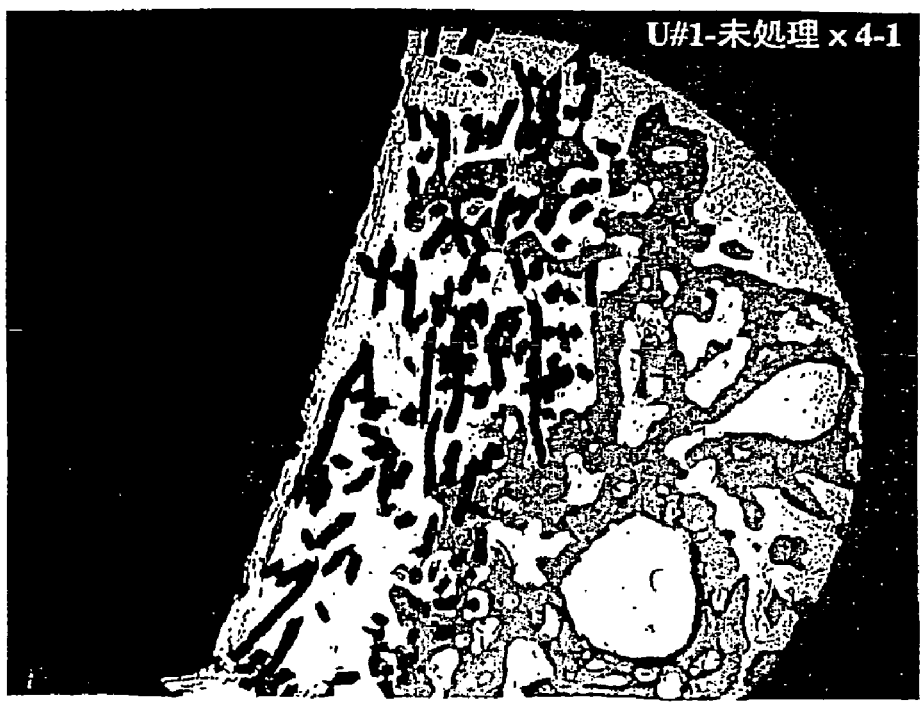
Figure 6:
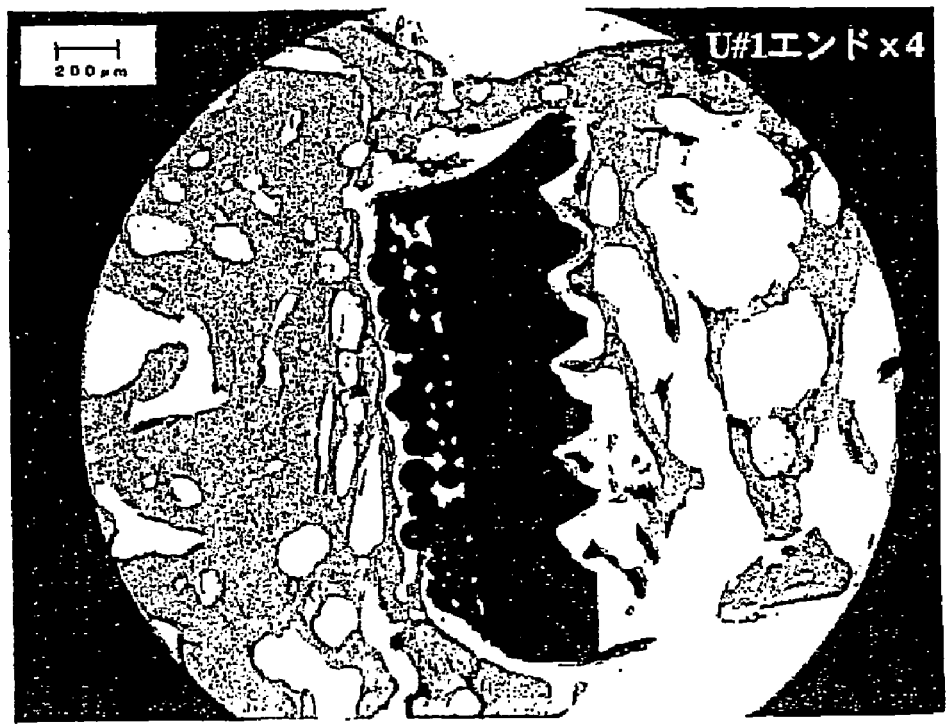
FIG. 6 is a microscopic observation showing state of bone formation when a specimen of a titanium implant, which equipped with titanium beads, was implanted into the defect of rabbit cranium (A), and a state of bone tissue formed by self-healing of the defect (B). Both microscopic pictures were observed after 4 weeks after operation.
Figure 6:

II. Experimental Results:

A tissue section specimen for microscope observation obtained in above item 3 is inspected by an optical microscope. Accordingly, following facts became clear as shown in FIGS. 5 (A) and (B) and in FIGS. 6 (A) and (B).
(i) In the case of a specimen which is prepared by equipping titanium non-woven cloth by 1 mm thickness around a titanium rod of 1.5 mm diameter and by carrying out hydroxyapatite coating with a liquid method and implanted in rabbit for 4 weeks, it is clearly observed that bone reaches to the deep part of titanium non-woven cloth layer and cover the surface of a titanium rod [FIG. 5 (A)].
(ii) In the composite prepared by equipping titanium non-woven cloth by 1 mm thickness around a titanium rod of 1.5 mm diameter and sintering in vacuum, and implanted without carrying out hydroxyapatite coating, it is clearly observed that bone formation does not grow sufficiently in titanium non-woven cloth part and is stopping at halfway [FIG. 5 (B)].
(iii) For the comparison, the experiment by a beads method, which is conventionally used, is carried out. That is, in the experiment implanting a titanium implant to which titanium beads are put on to a titanium rod (4 weeks passed), bone can not grow into the inside of titanium beads and remains at the outside [FIG. 6 (A)]. According to this result, the growth of bone into the inter bead spaces can not be expected at least in 4 weeks.
(iv) Further, for the comparison, a self-healing experiment is carried out. That is, a hole of 3 mm diameter and 2.5 mm depth is dug in a calvarial bone of a rabbit and left for natural healing [FIG. 6 (B)]. According to this drawing, it is obvious that the missing part of 3 mm diameter and 2.5 mm depth, which is indicated in majority part of upper right part of the drawing, is already filled by spongy bone and regenerated naturally after four weeks. Bone grows from the inner periphery to the center part of the circle. From experimental results, it is confirmed that in the case of an apatite coated titanium rod equipped with titanium non-woven cloth, bone migrates into whole layer of non-woven cloth and reaches to the surface of the rod, while, in the cases of other materials or treating methods, it is difficult to reach to the deep part.

Example 4

Example for Apatite Coating Treatment

Apatite treating liquid and a method for apatite coating:

Referring to the concentration of mineral in blood plasma of human, the treating liquid is prepared. Salts are added into distilled water so as the concentration of the treating liquid to become 5 times to blood plasma of human, then carbon dioxide gas is blown in through a ceramic filter, the salts are dissolved and pH of the liquid is adjusted to 6.01. The process is stopped at the point where all salts are dissolved and preserved in the atmosphere of carbon dioxide gas. This liquid is stable at the temperature of 37° C. for 1-2 weeks and does not generate precipitation. A titanium product to be coated is dipped in this liquid for 1 week, then observed by SEM.

The composition of the prepared liquid is shown below.

| | |
|---|---|
| Sodium ion: | 710 mM (millimoles per liter) |
| Potassium ion: | 25 mM |
| Magnesium ion: | 7.5 mM |
| Calcium ion: | 12.5 mM |
| Chlorine ion: | 720 mM |
| Bicarbonate ion: | 21 mM |
| Phosphate ion: | 5 mM |
| Sulfate ion: | 2.5 mM |

Carbonate ion is the saturated concentration at weak acidity (pH 6.01) at 37° C. by blowing in carbonate dioxide.

The above mentioned liquid composition is one example and not intending to be limited to this example. Various liquids which generate apatite are reported in many documents, and anyone of these liquids can be used in the present invention.

Figure 7:
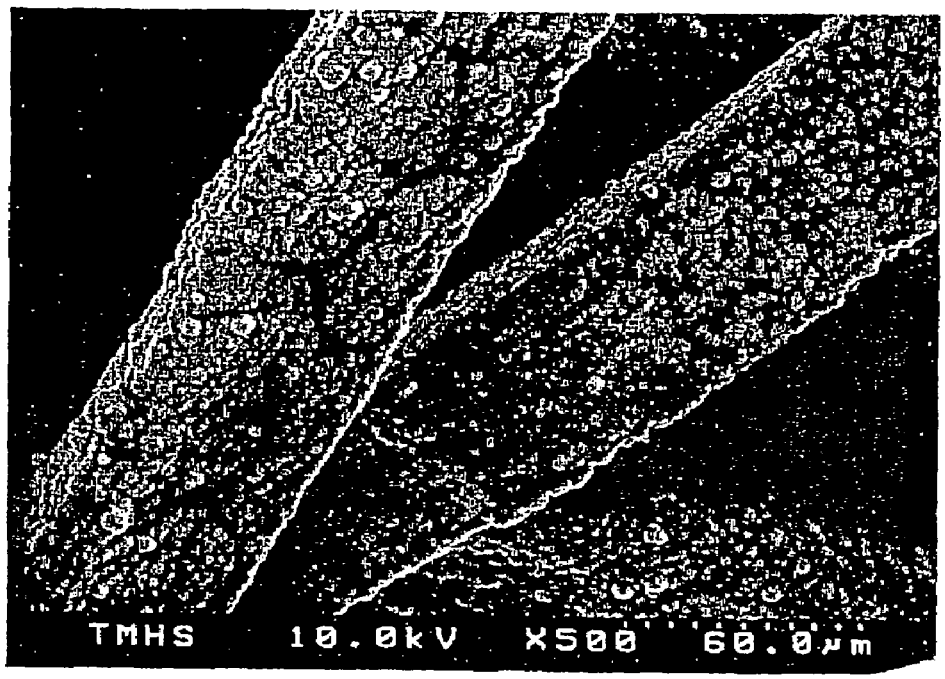
FIG. 7 is a drawing of the results by SEM observation of the surface of titanium fibers sintered with the titanium rod and with apatite coating (A), and the same materials as A, but without sintering on with titanium rod (B). There was no detectable difference between them.
Figure 7:
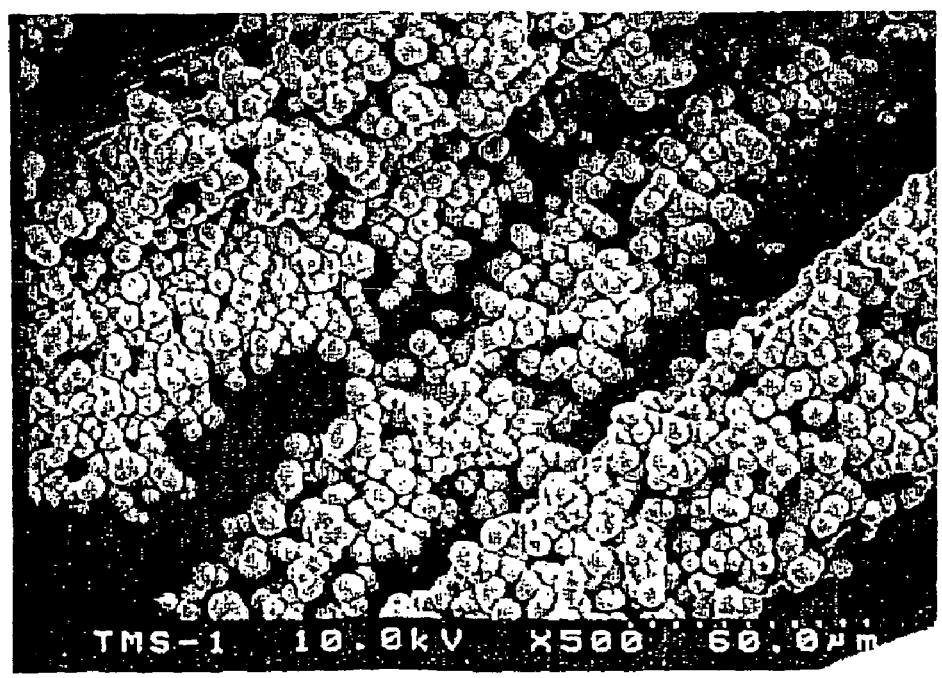
Figure 8:
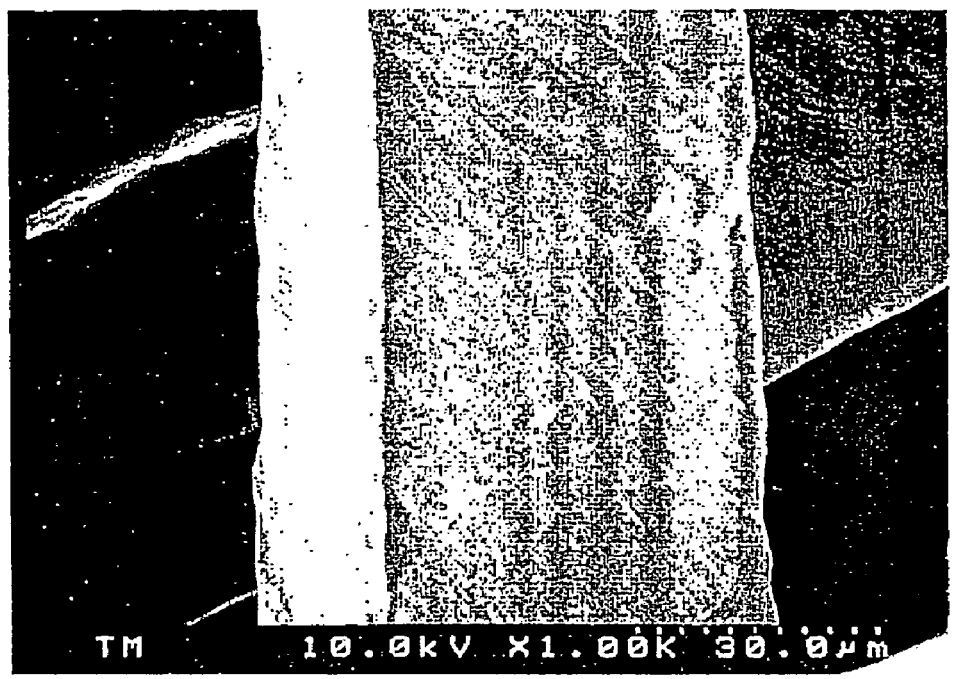
FIG. 8 is a drawing of the results by SEM observation of the surface of titanium fibers before (A) and after (B) sintering in vacuum. There was no detectable difference between them.
Figure 8:
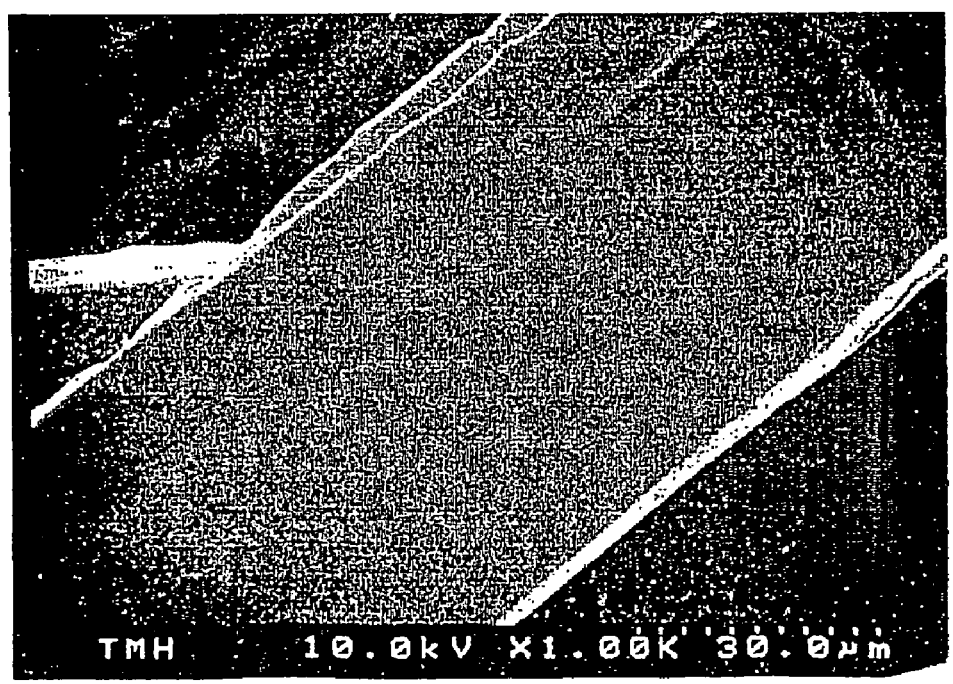

As a specimen of the titanium metal fibers layer which is dipped, (a) sintered in vacuum type and (b) not sintered in vacuum type are used and compared. Results are shown in FIGS. 7 (SEM pictures) (A) and (B). Deposition of fine crystal of apatite can be observed on the surface of both specimens, and there is no difference between two types, namely, sintered in vacuum and not sintered in vacuum. For the reference of this apatite coated titanium metal fiber non-woven cloth, the picture showing the state before coating is shown in FIG. 8. FIG. 8 (A) shows the titanium non-woven cloth before heat treatment and FIG. 8 (B) shows the titanium non-woven cloth after heat treatment.

Example 5

Comparison experiments for cell cultivation comparing a conventional cell cultivation substrate with a bioreactor using fiber layer consisting of non-woven cloth made of titanium fibers whose average diameter is smaller than 100 μm or less and aspect ratio is 20 or more regulated in the present invention;

Experimental method: Necessary numbers of cultivation wells of 16 mm diameter are prepared, (1) titanium non-woven cloth or (2) porous apatite block is laid at the bottom of wells and (3) for blank test, a well with plastic board to which no sheet is laid. Same numbers of osteoblast MC3T3EI, which is established in worldwide, are sown in each well. The numbers of proliferated cells after 1 week and 3 weeks are measured by DNA measurement and compared.

Figure 9:
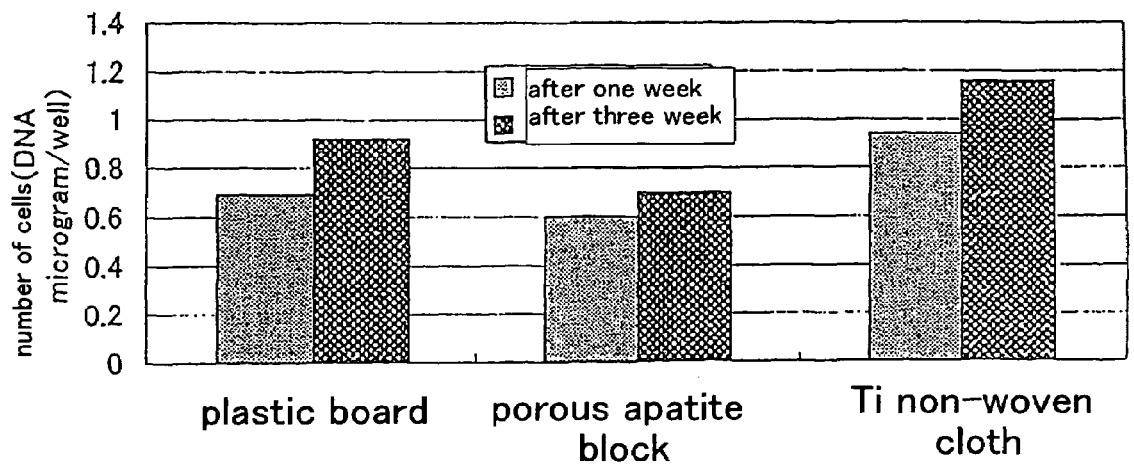
FIG. 9 is a drawing showing comparative experimental results of osteoblasts proliferation (A) and cytodifferentiation (B) by a bioreactor of present invention (right column), conventional porous apatite (middle column) and on a conventional plastic dishes (left column). Cell numbers were expressed by DNA contents.
Figure 9:
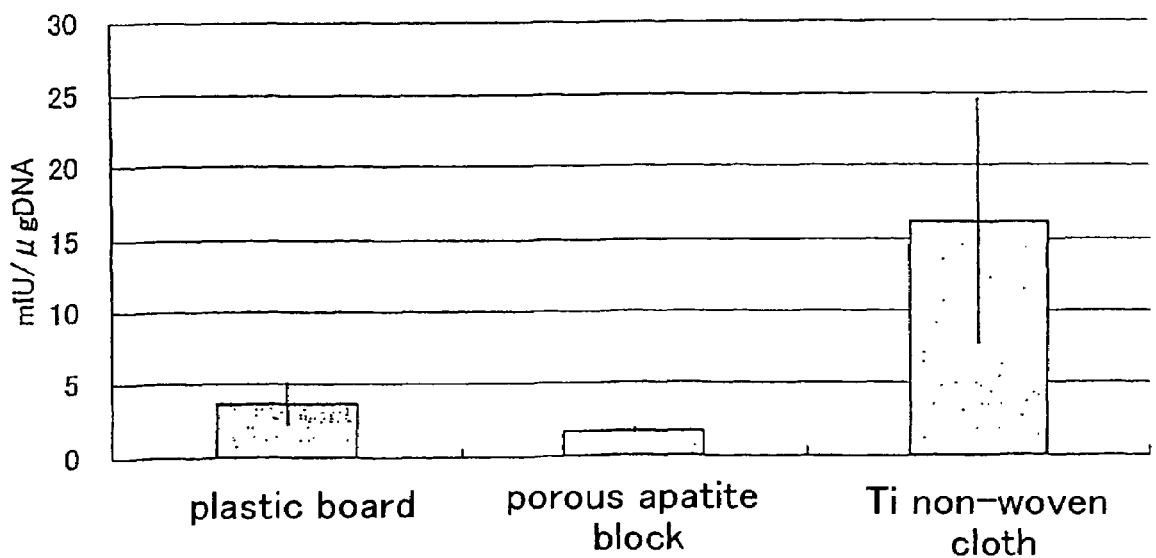

Experimental results: Results are summarized in FIG. 9. After 1 week the cells number increased to 1.4 times to that of plastic board and after 3 weeks increase to 1.3 times. On the contrary, a porous apatite block which is used as the conventional cell cultivation substrate has inferior cell cultivation ability than the plastic board. From said results, it can be said that the titanium non-woven cloth of the present invention is a very suitable substrate material for the mass cultivation of osteoblasts.

In above mentioned Examples, a scaffold material which indicates high affinity to osteoblasts is mainly disclosed, however, the present invention is also disclosing and providing a scaffold material which can be applied to cells besides bone cells and to living tissues, further a reactor material for cell cultivation and proliferation concerning all cells in regenerative medical engineering. This is clearly understood from these experiments and community of cells, and aforementioned $10^{th}$ to $12^{th}$ subjects, namely from item (10) to item (12) are carried out concerning those points.

A bioreactor has a very important position as a basic reaction device in life science in the circumstances where the development of artificial tissues and various organs are becoming to be realized and utilized. Considering these circumstances, the significance of the present invention is very big. The development of various regenerative medical engineering utilizing proliferation technique for stem cell, which is a current topic, and accompanying development of various tissues and organs which do not have after-effect contributes to the growth of medical science and welfare of human beings, and the present invention is taking part in said development and is greatly expected. That is, the object of the present invention is not limited to a biological hard tissue inductive or replacing scaffold material.

While, besides the aforementioned prior arts, techniques to fabricate a fiber layer using fibers or to form non-woven cloth of fibers and to induce living tissues into fiber gaps are proposed as an artificial blood vessel made from cloth and are presented in various papers, further published in many patent documents.

However, contents disclosed in these documents is not aiming at affinity of cells such as osteoblasts to materials, but aiming to reinforce the strength of blood vessel using fiber material and aiming natural filling of bonding tissue not to cause the leak of liquid from the inside of blood vessel. On the contrary, the present invention is requiring positive affinity with cells such as osteoblasts, therefore, titanium metal material is selected, especially, the specific fiber having very fine diameter of 100 μm or less is selected.

Regarding the trial to induce osteoblasts using metal fiber including titanium fiber, only there is a disclosure in Japanese Application Publication 8-140996 introduced in DESCRIPTION OF THE PRIOR ART. However, fine fiber disclosed in the document is a single filament whose diameter is from 0.1 mm to 0.7 mm diameter and is winded around a core. While, actually in the present invention, the titanium fiber is restricted to have 100 μm or less average diameter and to have lower limit of aspect ratio to 20 or more, and said fiber is used by entangling at random, therefore, space formed among these fibers is quite different from that of simple two dimensional space formed by conventional implanting method. That is, in the present invention, since cells are induced into the space formed by fibers and indicates high affinity, accordingly, proliferation speed is higher than that of the conventional method (3 to 6 months), and the formation of one body tissue can be observed after 4 weeks. Regarding this remarkably excellent action and effect of the present invention, however, in the said patent document, the reason why to provide metal filament is to expect buffering effect. There is no description teaching of various actions and effects such as generation of high affinity which is the unexpected effect of the present invention.

The technique to implant an artificial material into bone tissue and to fix it stable is very important to maintain mechanical function to the artificial organs, and without this technique, an artificial bone head (joint) or an artificial root of the tooth is unstable and releases soon. For the purpose to fix it stable, it is necessary that the interface between an implanted artificial material and bone is adhered without leaving gap and without interposing a tissue except bone or other subject, and required that the implanted subject and the bone to be chemically bonded strongly and not to be removed easily. Said connecting status between an implanted artificial material and bone is conventionally called as "osteoconduction" or "osteointegration", and the technique to obtain this status as soon as possible after implanting artificial subject in bone is strongly required by many clinicians, researchers and patients. However, as recited in clause of DESCRIPTION OF THE PRIOR ART of the present invention, from 3 months in earlier case and 6 months in later case are needed to accomplish stable osteointegration, and it is necessary to keep rest during this period, further during this period it is difficult to recover the function and is impossible to progress to the next medical treatment.

Scaffold, namely an implant of the present invention is to increase surface area and is to attempt to make bone and an artificial subject one body by prompting the migration of bone into inside and the formation of a hybrid layer consisting of bone and the implant as shown in FIG. 1(b). That is, as shown and illustrated in FIG. 1 (a), the present invention is quite different from the conventional two dimensional concept which adhere the surface of bone and the surface of an artificial implant. Three dimensional complicated space is formed by three dimensionally random entangled fibers and very rigid hybrid layer is formed in very short term of one month or less. Further, in said hybrid layer, since bone carries out metabolism in living state, it is stable from physiological view point, is durable to the outer force and combining natural reparation ability and can maintain the function of artificial viscera stable and semi-permanently.

Specifically, although the essential point of the present invention is already mentioned in SUMMARY OF THE INVENTION and in Examples, the essential point of the present invention will be summarized and illustrated again. Said titanium layer is prepared by winding titanium whose average diameter is 100 µm or less around a bar or a rod (as the typical cross sectional view of the bar or the rod, circular or oval shape can be mentioned, however, any shape including square or rectangular shape is possible and can be selected properly according to a diseased part and is not restricted) made of the same kind of titanium metal or titanium group alloy to said titanium fibers by proper thickness and sintered in vacuum so as the contacting points of fibers each other and contacting points of the fiber with the implant to be fused and to be fixed without the fibers to be moved. By said process, the bar or the rod becomes one body with the fiber layer and a rigid product is formed. As mentioned in Examples, said rigid product provides a scaffold material or a bio reactor which is effective not only to an osteoblast but also to other cells. That is, by the present invention, besides the growth of osteoblast to have complex three-dimensional structure, the proliferation of cells themselves is accelerated and the excellent action and effect that the osteointegration tissue can be accomplished in short term.

In the present invention, since a medical material made of metal which needs affinity with bone, especially, fusing by sintering in vacuum is recited as one of main embodiment, the present invention is disclosed as a medical material composed of the same kind of titanium metal, however, the present invention can be used as the other medical materials and not intending to eliminate them.

For example, when the medical material of the present invention is used with a hydrophilic material having biodegradable property, it is expected to form a host tissue by replacing a host tissue with said medical material after implanted in an organism, and is suited to form a hybrid type tissue composed of hydrophilic resin and cells.

Since the present invention is possible to involve various cell growing factors to a hydrophobic material, it is possible to display its virtue for the induction of cells, which is impossible for a normal hydrophilic resin. Therefore, it is possible to form a specific functional tissue in an organism by collecting many artificially intended cells.

Since the present invention is possible to involve various cell growth preventing factors to a hydrophilic material, it is possible to form an environment where cells can not stuck in an organism. By applying this specific property, the tissue which can not be covered by cells for a long time can be formed in an organism, and can provide a space to carry out the sensing of various sensors in an organism. That is, quite different embodiments of use can be provided.

INDUSTRIAL APPLICABILITY

1. The present invention is selecting very fine titanium fiber having a specific aspect ratio as a biological hard tissue inductive scaffold material used with various implants, forming random entangled fibers layer and inducing bone tissue into the inside of said titanium fibers layer, consequently makes it possible to form hybrid state possessing remarkably higher affinity of titanium with bone tissue compared with the conventional method applying a beads method or others. Namely, the present invention is to provide a medical material possessing very high affinity with bone tissue and the significance of the present invention is very large.

2. Further, by carrying out subsidiary means such as sintering treatment in vacuum for shape maintenance, conducting the apatite coating treatment to accelerate the induction of osteoblasts or loading various bioactive substance, the remarkable action and effect that the induction of bone tissue characterized that bone tissue and implant are becoming one body and not leave imcompatibility can be provided with good reappearance. Thus, the present invention is expected to effect broadly to the field of orthopaedic surgery or to the field of odontology, and the significance of it is very large.

3. The scaffold material of the present invention is not only superior to the conventional implanting method which is only a simple two dimensional growth and combination from the view point that the scaffold material of the present invention can progress the growth and development of cells three dimensionally, but also is proved that the growing and proliferating speed is superior to the conventional implanting method, therefore, can be evaluated greatly from this point. As repeatedly recited above, from the view point that the formation of osteointegration tissue is accomplished within one month, which is an unexpectedly short term from the conventional technique, by the present invention, that is, the present invention brings excellent effect and gospel both to a medical doctor and a patient at the actual medical spot and the significance of the present invention is very large.

4. Further, since the present invention provides a material having high affinity not only to an osteoblast but also to various cells in an organism, the present invention can be said to provide not only a medical material but also a subject which acts as a reactor for cultivation and proliferation of cells in regenerative medical engineering, and the present invention is expected to contribute to the development of new medical industry.

The invention claimed is:

1. An implant material comprising:
   an implant made of titanium or titanium alloy, and
   a plurality of titanium or titanium alloy fibers fixed at the periphery of the implant,
   wherein said titanium or titanium alloy fibers have an average diameter of less than 100 μm and an aspect ratio of 20 or more,
   wherein said fibers are accumulated at random to form a layer comprising a growth space for biological tissue from the surface of said layer to inside of said layer, and
   wherein said implant and said titanium or titanium alloy fibers are sintered together in vacuum so that the fibers are fused and fixed to each other at their crossing points and contacting points, and the fibers and the implant are fused and fixed to each other at their contacting point.

2. The implant material in accordance with claim 1, wherein a surface of said fibers is coated with calcium phosphate compound containing hydroxyapatite or carbonateapatite.

3. The implant material in accordance with claim 1, wherein the surface of said fibers is treated with a treating liquid comprising a physiological active material or a physiological activation promoter which activates cells.

4. The implant material in accordance with claim 3, wherein the physiological active material or the physiological activation promoter which activates cells is at least one selected from the group consisting of cell growth factor, cytokine, antibiotic, cell growth controlling factor, enzyme, protein, polysaccharides, phospholipids, lipoprotein or mucopolysaccharides.

5. The implant material in accordance with claim 1, wherein the implant is an artificial root of a tooth having a part embedded in said layer of titanium or titanium alloy fibers, and wherein the layer is integrally fixed to a periphery surface of the embedded part of said artificial root.

6. The implant material in accordance with claim 1, wherein the implant is an artificial joint having a part embedded in said layer of titanium or titanium alloy fibers, and wherein the layer is integrally fixed to a periphery surface of the embedded part of said artificial joint.

7. The implant material in accordance with claim 1, wherein the implant is an implant for bone repair having a part embedded in said layer of titanium or titanium alloy fibers and wherein the layer is integrally fixed to a periphery surface of the embedded part of said implant.

8. A method for forming an implant material comprising,
   forming a layer by entangling titanium or titanium alloy fibers having an average diameter of smaller than 100 μm and an aspect ratio is 20 or more, and
   combining the layer with an artificial root of a tooth or an artificial joint, and sintering it in vacuum so that the fibers are fused to each other at their crossing points and contacting points and the fibers and the artificial root or the artificial joint are fused and fixed to each other at their contacting point,
   wherein said artificial root or said artificial joint is made of titanium or titanium alloy.

9. The method for forming the implant material in accordance with claim 8, further comprising the step of treating the layer with apatite forming liquid after sintering.

10. The method for forming the implant material in accordance with claim 8, further comprising the step of treating the layer with a treating liquid comprising a physiological active material or a physiological activation promoter which activates cells.

* * * * *